United States Patent [19]

Goffinet

[11] Patent Number: 4,763,671
[45] Date of Patent: Aug. 16, 1988

[54] METHOD OF TREATING TUMORS USING SELECTIVE APPLICATION OF HEAT AND RADIATION

[75] Inventor: Don R. Goffinet, Stanford, Calif.

[73] Assignee: Stanford University, Stanford, Calif.

[21] Appl. No.: 858,891

[22] Filed: Apr. 25, 1986

Related U.S. Application Data

[63] Continuation of Ser. No. 565,505, Dec. 27, 1983, abandoned.

[51] Int. Cl.$^4$ .............................................. A61N 1/06
[52] U.S. Cl. .................................. 128/786; 128/804; 128/784; 128/1.2; 128/303.13
[58] Field of Search ................... 128/1.1, 1.2, 303.1, 128/303.13, 303.14, 303.17, 784, 786, 804

[56] References Cited

U.S. PATENT DOCUMENTS

| | | | |
|---|---|---|---|
| 623,022 | 4/1899 | Johnson | 128/786 |
| 3,230,957 | 1/1966 | Seifert | 128/804 |
| 3,411,507 | 11/1968 | Wingrove | 128/784 |
| 3,434,467 | 3/1969 | Anderson et al. | 128/1.1 |
| 3,474,791 | 10/1969 | Benton | 128/786 |
| 4,154,246 | 5/1979 | LeVeen | 128/786 |
| 4,244,357 | 1/1981 | Morrison | 128/1.2 |
| 4,346,715 | 8/1982 | Gammell | 128/804 |

FOREIGN PATENT DOCUMENTS

2105201  3/1983  United Kingdom ............... 128/804

Primary Examiner—Edward M. Coven
Attorney, Agent, or Firm—Flehr, Hohbach, Test, Albritton & Herbert

[57] ABSTRACT

A catheter for use in treating tumors is flexible and relatively small in diameter so that it can be inserted interstitially into the tumor mass. A conductor is provided along the length of the catheter and is electrically insulated except for a small length thereof which is adapted to be received within the tumor volume. By placing at least a pair of such catheters within the tumor mass and by connecting the conductors to a high frequency power source a heat producing current can be generated through the tumor tissue between the exposed portions of the catheter to damage the tumor cells. In addition, each catheter includes an axial passage permitting radioactive seeds or other tumor treating materials to be inserted within the tumor mass to cause further damage to and ultimately necrosis of the tumor without significantly affecting the adjacent healthy tissue of the body.

5 Claims, 2 Drawing Sheets

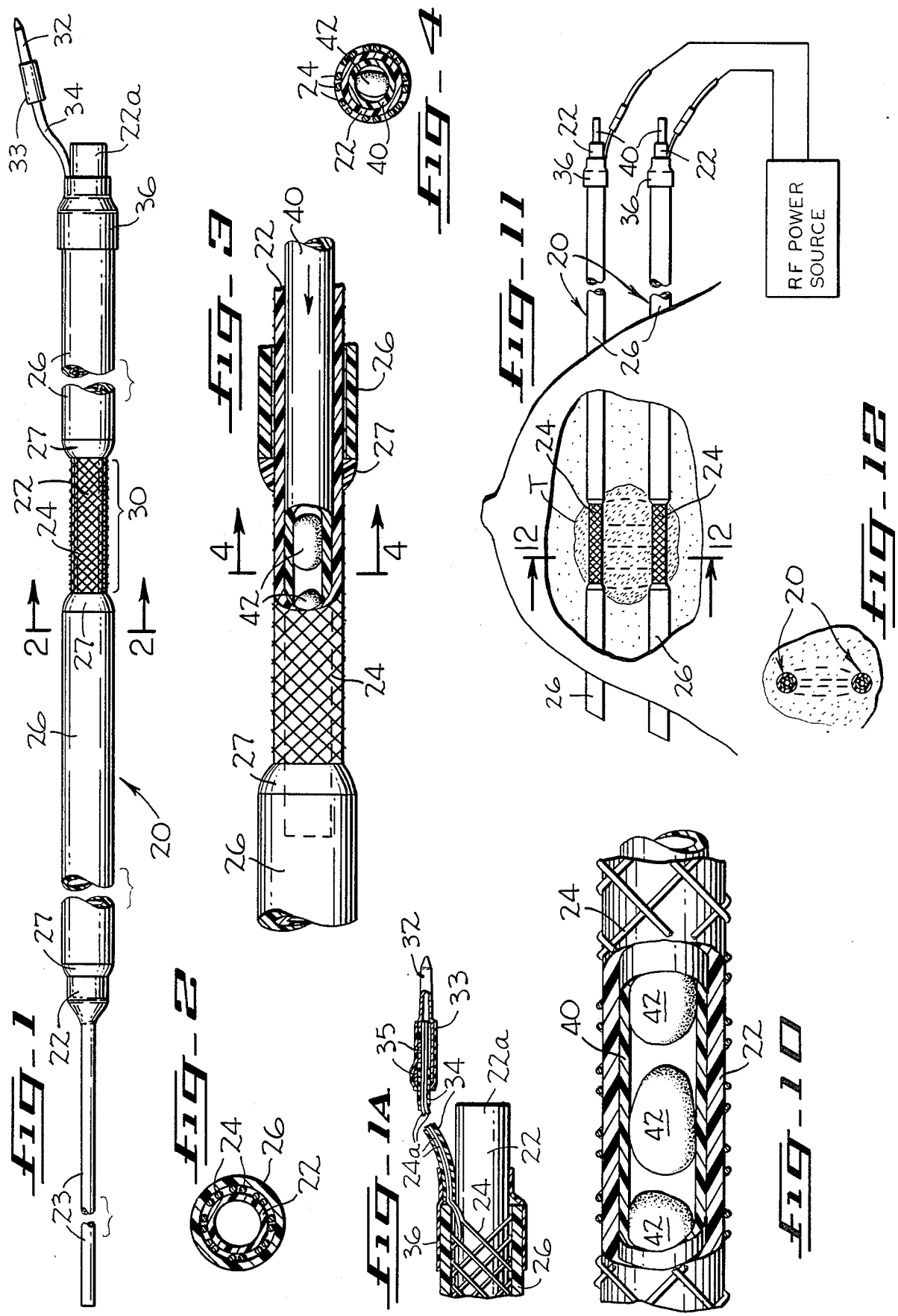

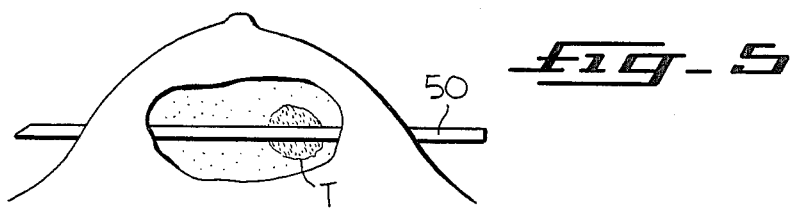
*fig_5*
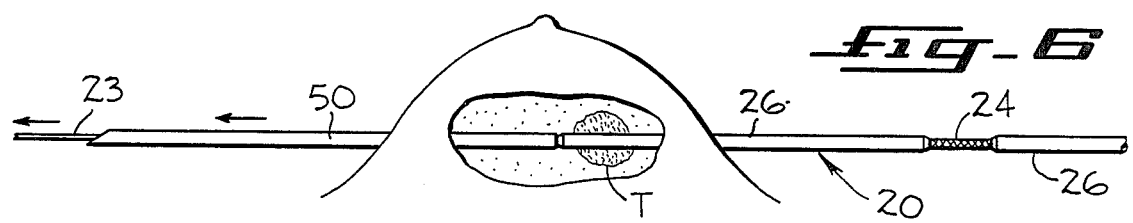
*fig_6*
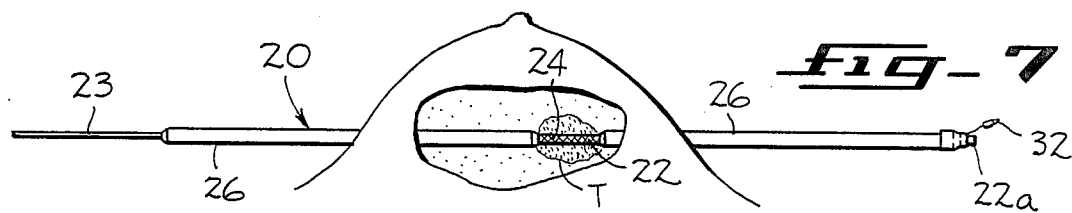
*fig_7*
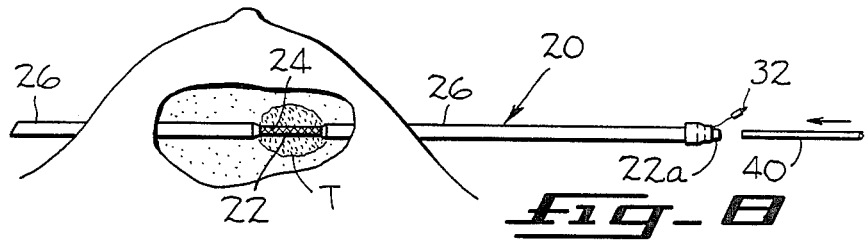
*fig_8*
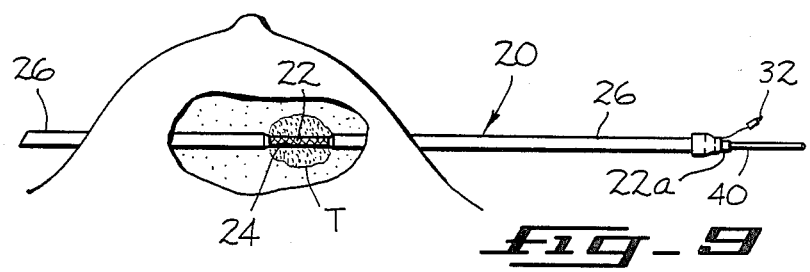
*fig_9*

METHOD OF TREATING TUMORS USING SELECTIVE APPLICATION OF HEAT AND RADIATION

This is a continuation of application Ser. No. 565,505 filed Dec. 27, 1983, now abandoned.

BACKGROUND OF THE INVENTION

1. Field of the Invention

The present invention pertains to means and methods for treating tumors, and more particularly malignant tumors, in the bodies of animals, such as humans, and more particularly, it pertains to means and methods which utilize the application of a controlled heat source to the tumor volume to cause or aid in the cause of its necrosis.

2. Description of the Prior Art

In the treatment of malignant tumors in humans, it is well known that the controlled application of heat can be used to kill the malignant tumor cells. Being able to apply such heat to the tumor volume for a sufficient period of time and at an intensity to cause necrosis of the malignant cells without severely damaging the surrounding healthy tissue of the patient has always been a problem. Typically, by using ultrasound and electromagnetic heating techniques, heat can be radiated from the surface of the skin to a depth of about 3 cm. Such electromagnetic heating has been combined with radiation treatment for tumors to achieve some satisfactory results, and various configurations of prior art devices have been used in such prior art cancer treatment methods.

Most of the prior art hyperthermia treatment apparatus are comprised of non-invasive devices for use on the skin surface; however, because of the depth limitations of surface heating methods, invasive devices have also been utilized in the prior art to provide the heat source at the tumor site. Thus, in U.S. Pat. No. 4,154,246 to LeVeen a tuned coil is disclosed which is capable of being inserted into the tumor volume whereby the external application of a strong electromagnetic field creates electromagnetic radiation from the coil which is presumably sufficient to cause necrosis of the tumor.

U.S. Pat. No. 4,106,488 to Gordon discloses a process wherein minute ferromagnetic particles are placed in the tumor volume and then are inductively heated by subjecting them to a high frequency alternating electromagnetic field. These particles can, in addition to their use as radiating heat centers, also incorporates specific radioisotopes or tumor specific antibodies which are arranged to be released upon the generation of the heat to further aid in destroying the malignant cells.

U.S. Pat. No. 4,292,960 to Paglione discloses an invasive device which is adapted to generate microwave energy and which also includes radioactive material for application to the internal organs of the human body.

Finally, U.S. Pat. No. 2,102,270 to Hyams discloses a device wherein a tiny electrode is inserted into the tissue of a body and then a strong high frequency electrical current is generated between the electrode and an external elelctrode so as to pass an alternating current through the body in a narrow path to perform electrosurgical operations of the like.

Additionally, hyperthermia treatment of tumors has been done by connecting a pair of stainless steel tubes to a high frequency power source, and inserting the tubes into the tumor. Current passing between the tubes thus passes through the tumor to destroy the malignant cells thereof. However, the current also passes through the patient's flesh at portions of the tubes other than in the tumor volume, and therefore these devices have not proved to be too useful since they can cause significant damage to the healthy tissue of the patient.

Another conventional method of treating malignant tumors through the use of radioactive materials is to insert a catheter having an axial passage into the patient so that it passes into the tumor volume. A tube containing a number of radioactive seeds is then insertd into the axial passage of the catheter until the seeds are located adjacent the tumor site. The tubular insert is then left in the patient for a predetermined amount of time in order to permit the radioactivity to cause necrosis of the tumor cells.

SUMMARY OF THE INVENTION

By the present invention, a catheter is provided which can be invasively used to treat tumors within the body of animals such as humans. The catheter generally comprises an elongate flexible member relatively small in diameter so that it can be inserted into the interstitium of a patient with a minimum of damage being done to the surrounding tissue by insertion and subsequent removal of the catheter and with a minimum of discomfort to the patient while the catheter is in place. The catheter is comprised of a supporting member having an axial passage extending therethrough and a relatively low density conductor which extends along the outer circumferential surface of the supporting member. Insulation is provided about the exterior of the catheter so as to leave exposed at least one portion of the conductor which portion shall be arranged to be located in or directly adjacent to the tumor site when the catheter is inserted in the patient. The conductor, at one end of the catheter, is provided with means to connect it to a source of relatively high frequency current which current is directed from the exposed conductor portion through the tumor to a similar electrode or to an external electrode also connected to the high frequency current source. By means of the axial passage in the catheter, additional material to aid in destroying the tumor, for example, radioactive seeds, may be inserted along the catheter and located at the tumor site for predetermined periods of time.

In the preferred method of treating a tumor, two of the aforedescribed catheters are placed within the tumor volume and a high frequency alternating current is directed between them so as to selectively heat the tumor tissue to cause damage to the tumor cells without significantly affecting the adjacent healthy tissue of the body.

With the comfortably indwelling, minimally invasive, small diameter catheters of the present invention, the patient will suffer a minimum of discomfort during the tumor treatment. Thus, the catheters may be left in the patient's body for the duration of the treatment, and selective hyperthermia and/or radiation treatment may be obtained as desired in a highly effective and carefully controlled manner whereby minimal damage is done to the surrounding healthy tissue of the patient.

BRIEF DESCRIPTION OF THE DRAWINGS

FIG. 1 is a side elevation of the catheter of the present invention with portions thereof being broken away to reduce the overall length of the device.

FIG. 1A is an enlarged axial section of the right-hand end of the catheter of FIG. 1 particularly showing the electrical conductor power connection.

FIG. 2 is an enlarged section taken on line 2—2 of FIG. 1.

FIG. 3 is an enlarged detail view, partially in section, of the conducting electrode portion of the catheter of FIG. 1 and including the insertion of a radioactive material containing tube along the central axial passage of the catheter.

FIG. 4 is a section taken on line 4—4 of FIG. 3.

FIGS. 5–9 are sequential diagrammatic illustrations of the manner in which the catheter is placed within the body of a patient and is utilized to provide treatment of a malignant tumor volume.

FIG. 10 is an enlarged side elevation, partially in section, of the exposed electrode portion of the catheter of the present invention with the radioactive seed tube in place within the axial passage of the catheter.

FIG. 11 is a diagrammatic illustration showing a pair of catheters connected to a power source and being utilized to provide tumor treatment in a patient.

FIG. 12 is a section taken on line 12—12 of FIG. 11.

DESCRIPTION OF THE PREFERRED EMBODIMENT

A preferred form of the catheter 20 for performing the tumor treatment operations is shown in FIG. 1. Referring now to such Figure as well as to the detail FIG. 1A and to the cross-section shown in FIG. 2, it will be seen that the inner supporting member 22 of the catheter is cylindrical in shape. This supporting member is formed of a relatively hard plastic material. One end 23 of the tubular supporting member 22 is reduced in diameter for a purpose which will be explained presently.

Received tightly about the outer circumferential surface of the supporting member 22 is a conductor 24 which, in the present case, is in the form of a relatively open mesh, i.e., wherein the conductor covers only a relatively small portion of the circumferential area of the surface of the supporting member (as shown in FIGS. 3 and 10). A circumferential layer of insulation 26 tightly surrounds the conductor and is secured thereto by means of adhesive beads 27 so as to completely cover all of the conductor except for a preselected length 30 at a predetermined position along the length of the catheter. Thus, the conductor is left exposed only in one relatively short section wherein conduction of an electrical current from the conductor will occur. In general, the length 30 of the conducting electrode portion of conductor 24 will be sized to fit the size of the tumor to be treated. Thus, catheters having various different lengths 30 of exposed electrode may be provided with individual ones of such catheters being selected for use depending on the size of the tumor to be treated. Alternatively, the insulation 26 may initially cover all (or almost all) of the length of the catheter and it may be selectively removed just prior to use to expose the correct length 30 for use in the particular tumor to be treated.

One end of the mesh conductor 24 is unravelled and formed into a braid 24a that is connected to a male electrical power connector 32 for plugging into a high-frequency power source, the details of such connection being shown in FIG. 1A. As therein shown, the unravelled and braided end 24a of the conductor mesh 24 is directed outwardly of the catheter and is provided with a shrink tubing protective wrapping 34. The adjacent end of the catheter (with the exception of a projecting portion 22a of the inner tubular supporting member 22) and the attached end of the sleeve 34 are tightly wrapped in a piece of shrink tubing 36. The outer end of the braided lead 24a is secured to the power connector 32 by means of one pair of tangs 35 which clamp the inner end of the connector to the sleeve 34 and a further pair of tangs 35 which are crimped directly into the end of the lead 24a. A piece of shrink tubing 33 is wrapped about this crimped connection to insulate it.

As will be recognized, all of the materials of the catheter 20 which are to be inserted into the body of a patient must be made of non-toxic, non-carcinogenic materials while at the same time they must be flexible and resilient and quite tough so as to resist shredding or breakage. Thus, in the preferred embodiment of the invention, the inner tubular supporting member 22 is formed of a thin walled polyethyleneterapthalate material. The adhesive to secure the electrical insulation about the outer surface of the catheter is preferably a 724-1 urethane adhesive, and the electrical insulation is formed of a suitable polyethylene with a wall thickness of approximately 0.005 inches to 0.008 inches.

Care must be taken in selecting the configuration and material for the conductor 24 since such a conductor must (1) have high electrical conductivity, (2) have a relatively low atomic number (so that radioactive material placed in the catheter during subsequent radiation treatment will not be unduly attenuated by the overlying conductor), (3) be formed of a biocompatible material, and (4) be formed of a tough, nonbreakable material which will resist breaking even at very small diameters and considerable bending and flexing during implantation and removal from the body of a patient. Also, the relative density of the conductor in cross-section must be low so as to minimize the amount of thermal conductivity. That is to say, when the tumor tissue adjacent to the conductor is heated by passing the electrical current therethrough, it is important that the heat conducted away from such tumor by the conductor itself be minimized to the extent possible. Thus, as can be seen from FIGS. 3, 4 and 10, the amount of metal in an average cross-section through the conductor is relatively low and the amount of open area not covered by the wires of the mesh is high as compared to the area covered by the mesh. The material found to be best adapted to the foregoing requirements is a mesh of 0.004 inch diameter nickel wire having a 26 pick. This material has electrical conductivity great enough so as to not be unduly heated by the conduction of the requiste alternating currents therethrough. Also, the thickness of the wire mesh and the relatively wide spacing of the individual wires provide a minimum of contact with the tumor tissue for promoting thermal conductivity.

As mentioned hereinbefore, it is important that the catheter be of as small a size as possible and highly flexible so that it can be placed into the body of a patient and so that it can remain there throughout the course of treatment which may require several weeks. In the preferred embodiment of the invention shown, the outer diameter of the catheter 20 including the insulation 26, is arranged to be approximately 0.08 inches with the diameter of the axial passage through the supporting member 22 being in the order of 0.04 inches for receiving material to further aid in the tumor treatment operation.

In order to further aid in such tumor treatment, a tubular sleeve 40 (FIGS. 3, 4 and 10) including radioactive seeds 42 of iridium or the like located therein is adapted to be inserted within the central axial passage in the support member 22 as, for example, through the open end 22a thereof. The length wherein the radioactive seeds 42 are provided in the tube 40 (which will generally correspond to the length 30 of the exposed portion of conductor 24) is shifted axially along the catheter until it precisely coincides with the exposed conductor portion 30. As will be explained in greater detail hereinafter, the hyperthermy treatment utilizing the electrical conductor 24 and the radiation treatment utilizing the radioactive seeds 42 in the insertable tube 40 can be conducted simultaneously, or, they may be conducted in tandem as, for example, first heating, then using an extended period of radiation treatment, and then reheating the tumor tissue immediately upon removing the radioactive material.

The manner in which the catheter is adapted to be implanted in the patient is shown diagrammatically in the illustrations of FIGS. 5 through 9. Thus, as shown in FIG. 5, a hollow needle, or trocar, 50 is first inserted into the patients's skin and through or directly adjacent to the tumor volume T. The necked down portion 23 of the supporting member 22 is then threaded into the trocar until the fully expanded portion of the supporting member 22 abuts against the end of the needle. The trocar 50 and catheter 20 are then pulled through the patient in unison with the main body of the catheter being dragged behind the trocar into the tumor area—as shown in FIG. 6. This operation is continued until the exposed length 30 of the conductor 24 is located so as to generally coincide with the diameter of the tumor T (FIG. 7). In order to prevent the catheter from being pulled completely through the initial insertion in the skin or body portion, an enlarged stop member (not shown) may be positiond about the catheter and secured thereto near the end 22a thereof. The exposed end of the catheter which has been pulled through the body of the patient with the trocar is then cut off, as shown in FIG. 8. Thus, in the operation illustrated in FIGS. 5-9, the radioactive seed containing tube 40 can be pushed into the catheter from either end thereof, i.e., either through the exposed end 22a at the electrical connection or through the cut-off end. It will be recognized, however, that in many intances one end will not be in a position to receive the insert. Thus, when the catheter is inserted deep within a patient as, for example, by initially opening a cut through the abdomen or stomach wall, the inserted end may wind up being left within the patient wherein no access is possible once the catheter implantation operation is finished and the patient has been sewn up again. Also, the end 22a of the supporting member 22 may be left in a location wherein insertion of the tube 40 is inconvenient and/or dangerous. Continuing with the operation shown in FIGS. 5-9, it will be seen from FIGS. 8 and 9 that the radio active seed containing tube 40 is pushed into the end 22a of the catheter until the seeds therein are positioned adjacent the tumor T and the exposed electrode 24. In practice, the implantation of the catheter is accomplished first, and the hyperthermy operation and the insertion of the radioactive material is accomplished at some later time.

In utilizing the catheters of the present invention, it is desirable to use at least a pair of catheters, both implanted in the patient in the manner shown in FIGS. 5 to 9, with the catheters being arranged generally in a parallel relationship and closely spaced (1-3 cm) within the tumor volume. such an arrangement is shown in FIG. 11 wherein it will be seen that each of the catheters 20 is connected to a radio frequency power source so that a high frequency alternating voltage is generated across the exposed portions 30 of the conductors 24 of each catheter with the current thus being required to pass through the tumor tissue adjacent the exposed portions 30 of the catheter. As shown by the dashed lines in FIGS. 11 and 12, this creates an electric field directly between the exposed electrode portions of the catheters which, due to the high electrical resistance of the neoplasm of the tumor, generates a considerable amount of heat. The heat thus generated can be maintained for a sufficient period of time to render the tumor susceptible to other treatment, i.e., radiation, or it can be left for a sufficient period of time to in and of itelf cause necrosis of the tumor tissue.

In utilizing the electrodes of the catheters of the present invention for hyperthermy treatment, it is important that the high frequency source be of a high enough frequency, i.e., 100 kiloHertz or higher, so that no excitation of the muscle tissue within the patient is created and only heat is generated. Thus, all of the available power is used in direct heating of the tumor tissue. Typically, the alternating current will be in the range of from about 0.5 mHz to about 30 mHz with a sufficient power level and with electrode spacing of 1 to 3 cm to raise the flesh temperature from the normal 37 degrees C. to something in the range of 42 to 44 degrees C. In treatments successsfully used thus far, a plurality of catheters have been inserted into a malignant tumor volume in the manner shown wherein temperatures of approximately 43 degrees C. were maintained in the tumor volume by means of generating electric current through the neoplasm in the manner shown for a period of about 45 minutes. Immediately thereafter, heat was removed and the iridium seed containing tubes 40 were inserted into the malignant volume for periods of approximately 60 hours. Immediately upon removal of the radiation, the malignancy was again electrically heated in the manner aforedescribed for a period of approximately 45 minutes. As will be pointed out in the specific examples presented hereinafter, this combined hyperthermia and radiation treatment of malignant tumors has had very beneficial effects thus far.

In one example of the use of the method of the present invention, a 41-year old man with a deeply invasive, massive adenoid cystic tumor on the base tongue and adjacent oropharygneal wall was provided with combined hyperthermia and radiation (brachytherapy) in conformance with the method of the present invention. Thus, eight catheters in two parallel rows were implanted in the tumor volume. The four catheters in each row were spaced one centimeter apart and there was a two centimeter spacing between the rows with the catheters being arranged in uniform opposed positions. The tumor was then heated to approximately 43 degrees C. and maintained at such temperature for approximately 45 minutes by selectively and sequentially connecting various pairs of the catheters to the high frequency power source for five second time periods in a manner so as to maintain a generally uniform temperature throughout the tumor. Immediately following the heat treatment, iridium (192) seeds were inserted within the catheters in the tumor in the manner previously described. The 192Ir seeds were left in the catheters for 50 hours, and immediately upon their removal the hyperthermy treatment (43 degrees C. for 45 minutes) was again provided. The radioactive sources provided 40 rads per hour or a total of 2,000 rads over the 50 hour treatment period. Upon examination approximately one month later, the tumor had disappeared and there was no further evidence of cancer.

In a second example, a 75-year old man had a medistatic carcinoma in the sacral hollow. In this case 5 catheters were implanted at 1 cm. (center-to-center) spacings in a plane through the malignant tumor mass. Again, the tumor was heated to 43 degrees C. for 45 minutes prior to loading of the iridium (192Ir) seeds. The iridium seeds were left in the catheters for 80 hours, giving approximately 4,000 rads of radiation total. Upon removal of th radioactive seeds, a repeat of the 45 minute (43 degree C.) hyperthermia was provided. As with the prior example, uniform heating was maintained in the tumor area at the proper temperature (43 degrees C.) by locating thermistors within the tumor mass to monitor the temperature, and by selectively and sequentially switching (at five second intervals) the radio frequency current source between selected pairs of catheters as necessary in order to maintain as uniform a temperature as possible throughout the tumor mass. Following the aforedescribed treatment pain relief was obtained, indicative of a favorable response to the treatment.

Although the best mode contemplated for carrying out the present invention has been herein shown and described, it will be apparent that modification and variation may be made without departing from what is regarded to be the subject matter of the invention.

I claim:

1. A method of treating a tumor in an animal, such as a human, comprising the steps of inserting a plurality of flexible catheters each containing an external electrode into a volume of the body of the patient in which the tumor is located, passing an electrical current from one catheter electrode to another electrode and defining an electrical current path through the tumor to thereby create selective heating of the tumor, inserting radioactive material in at least one of said catheters while said catheter remains in the body of the patient with the material being inserted at a location adjacent said tumor, and maintaining said current and said radioactive material in place for sufficient times to cause necrosis of said tumor without significantly affecting the adjacent healthy tissue of said body.

2. A method of treating a tumor according to claim 1 wherein said electrical current is applied first immediately before the insertion of the radioactive material and wherein the electrical current is applied again immediately after the removal of the radioactive material.

3. A method of treating a tumor in an animal, such as a human, comprising the steps of inserting a plurality of flexible catheters each containing an external electrode into a volume of the body of the patient in which the tumor is located, passing an electrical current from one catheter electrode to another electrode and defining an electrical current path through the tumor to thereby selectively heat the tumor for a period of time sufficient to sensitize the tumor cells and hinder any subsequent repair, immediately thereafter inserting radioactive material into at least one of said catheters while the catheter remains in the body of the patient with the material being inserted at a location adjacent said tumor, leaving the radioactive material in the catheter for a period of time sufficient to cause necrosis of said tumor cells, removing the radioactive material from the catheter, and immediately thereafter reapplying the electrical current through the tumor for a period of time sufficient to hinder any repair of the radioactively damaged tumor cells.

4. A method of treating a tumor according to claim 3 wherein said electrical current is passed through the tumor for periods of time of from about 30 minutes to about 60 minutes before and after the radioactive treatment, and wherein the radioactive material is in said catheter for a period of time of from about 48 to about 120 hours.

5. A method of treating a tumor according to claim 3 wherein the electrical current treatment periods are about 45 minutes each and wherein the radioactive material treatment period is about 60 hours.

* * * * *